US 9,521,950 B2

(12) United States Patent
Verdooner

(10) Patent No.: US 9,521,950 B2
(45) Date of Patent: *Dec. 20, 2016

(54) APPARATUS AND METHOD FOR IMAGING AN EYE

(71) Applicant: NeuroVision Imaging LLC, Sacramento, CA (US)

(72) Inventor: Steven Roger Verdooner, Granite Bay, CA (US)

(73) Assignee: NeuroVision Imaging LLC, Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/251,631

(22) Filed: Apr. 13, 2014

(65) Prior Publication Data
US 2014/0218687 A1    Aug. 7, 2014

Related U.S. Application Data

(63) Continuation-in-part of application No. 15/053,934, filed on Mar. 22, 2011, now Pat. No. 8,714,743.

(60) Provisional application No. 61/316,677, filed on Mar. 23, 2010.

(51) Int. Cl.
*A61B 3/14*    (2006.01)
*A61B 3/10*    (2006.01)
*A61B 3/00*    (2006.01)

(52) U.S. Cl.
CPC .............. *A61B 3/0058* (2013.01); *A61B 3/14* (2013.01)

(58) Field of Classification Search
USPC ............................................... 351/200–246
See application file for complete search history.

(56) References Cited

U.S. PATENT DOCUMENTS

| 7,854,510 | B2 * | 12/2010 | Verdooner et al. ........... 351/214 |
| 8,639,779 | B2 | 1/2014 | Carnevale |
| 8,783,866 | B2 * | 7/2014 | Hart et al. .................... 351/206 |
| 2003/0206272 | A1 | 11/2003 | Cornsweet |
| 2006/0292190 | A1 * | 12/2006 | Matier et al. ................. 424/400 |

(Continued)

FOREIGN PATENT DOCUMENTS

| DE | 102006038911 A1 | 2/2008 |
| WO | 2006118560 A2 | 11/2006 |

OTHER PUBLICATIONS

Corresponding European Office Action dated Oct. 3, 2014.

*Primary Examiner* — Mohammed Hasan
(74) *Attorney, Agent, or Firm* — Lucas & Mercanti, LLP; Peter J. Phillips

(57) ABSTRACT

A slit lamp mounted eye imaging, a slit lamp integrated, a handheld, OCT integrated, or attached to a separate chinrest-joystick assembly apparatus and method for producing a wide field and/or magnified views of the posterior or the anterior segments of an eye through an undilated or dilated pupil is disclosed. The apparatus images sections and focal planes and utilizes an illumination system that uses one or more LEDs, shifting optical elements, flipping masks, and/or aperture stops where the light can be delivered into the optical system on optical axis or off axis from center of optical system and return imaging path from the eye, creating artifacts in different locations on the eye image. Image processing is employed to detect and eliminate artifacts and masks from images. The apparatus can be used in combination with an OCT, microscope and can be disposed in a hand-held housing for hand-held use.

15 Claims, 10 Drawing Sheets

(56) References Cited

U.S. PATENT DOCUMENTS

2010/0316276 A1    12/2010   Torti
2013/0173750 A1    7/2013   Carnevale
2014/0218687 A1    8/2014   Verdooner

* cited by examiner

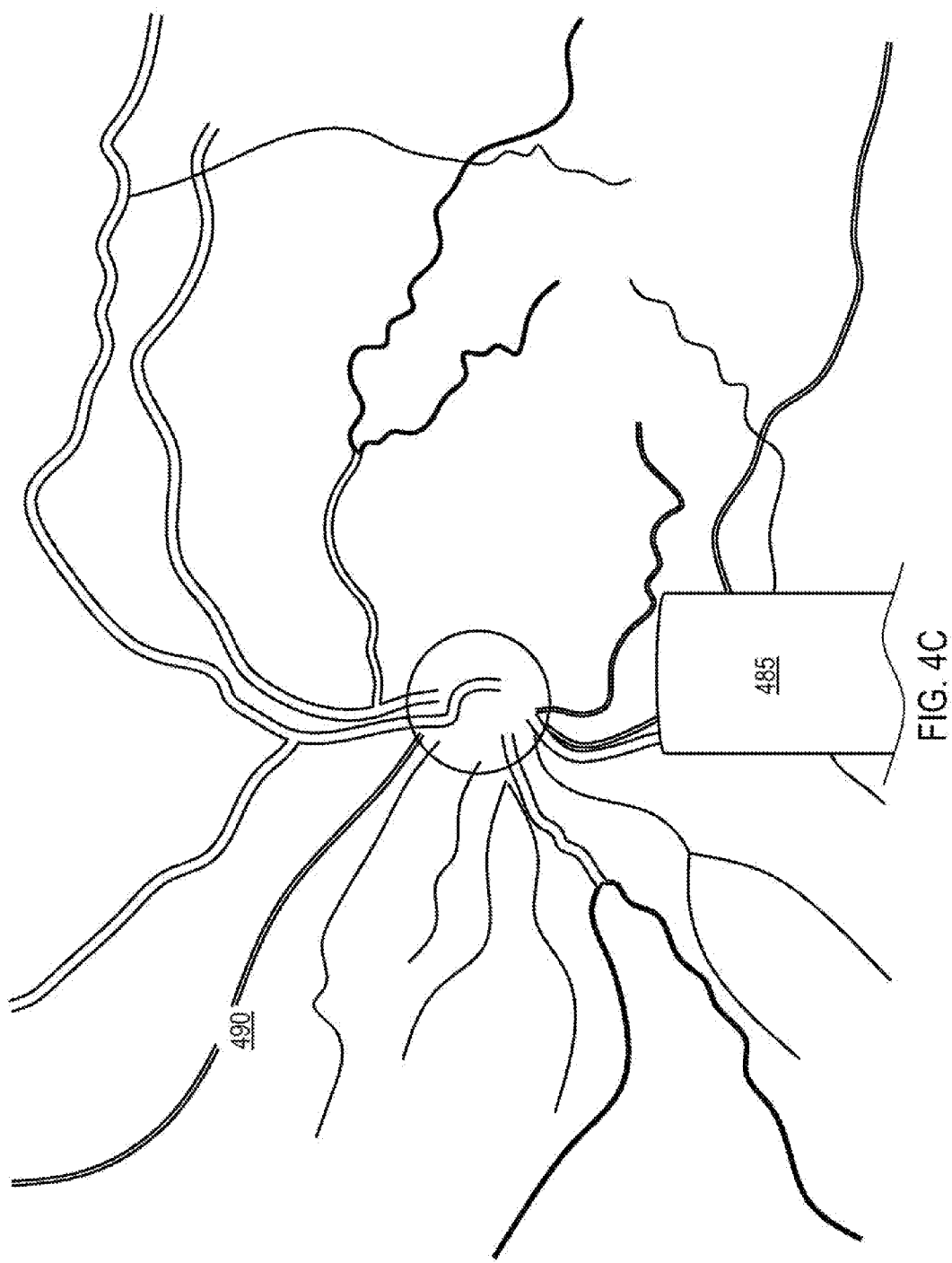

APPARATUS AND METHOD FOR IMAGING AN EYE

The present application is a Continuation-In-Part application to U.S. Non-Provisional application Ser. No. 13/053,934 filed on Mar. 22, 2011 Now U.S. Pat. No. 8,714,743 B2. The present application claims priority to U.S. Provisional Application 61/316,677 filed on Mar. 23, 2010, both disclosures are incorporated by reference herein.

TECHNICAL FIELD & BACKGROUND

Imaging the eye is challenging with regard to obtaining images that are of good quality, that include a wide field of view, that are free of central and other artifacts, that are in stereo, that can be obtained with ease of operator use, that can achieve proper alignment, focus and exposure for both dilated and undilated pupils in the posterior and anterior segments of the eye.

The present invention generally relates to a system and method for imaging an eye. The present invention provides a combination of innovative optical, mechanical, and image processing techniques that include utilizing optical technologies combined with various image processing techniques to obtain artifact-free images. More specifically, the invention is a system and method for imaging an eye that can be utilized in different operating modes and configurations that include a hand-held, microscope-mounted, integrated with optical coherence tomography (OCT) devices, integrated with direct and indirect ophthalmoscopes, a slit lamp mounted, a slit lamp integrated or attached to a separate chinrest-joystick assembly (fundus camera) configuration included with a plurality of accessories. The invention is able to image patients free of optical and other artifacts and also achieve wide field of view compared with current fundus cameras and other eye imaging devices.

BRIEF DESCRIPTION OF THE DRAWINGS

The present invention will be described by way of exemplary embodiments, but not limitations, illustrated in the accompanying drawing in which like references denote similar elements, and in which:

FIG. 4C illustrates a front perspective view of a flipping mask on an eye image capture, in accordance with one embodiment of the present invention.

DETAILED DESCRIPTION OF ILLUSTRATIVE EMBODIMENTS

Figure 1A:
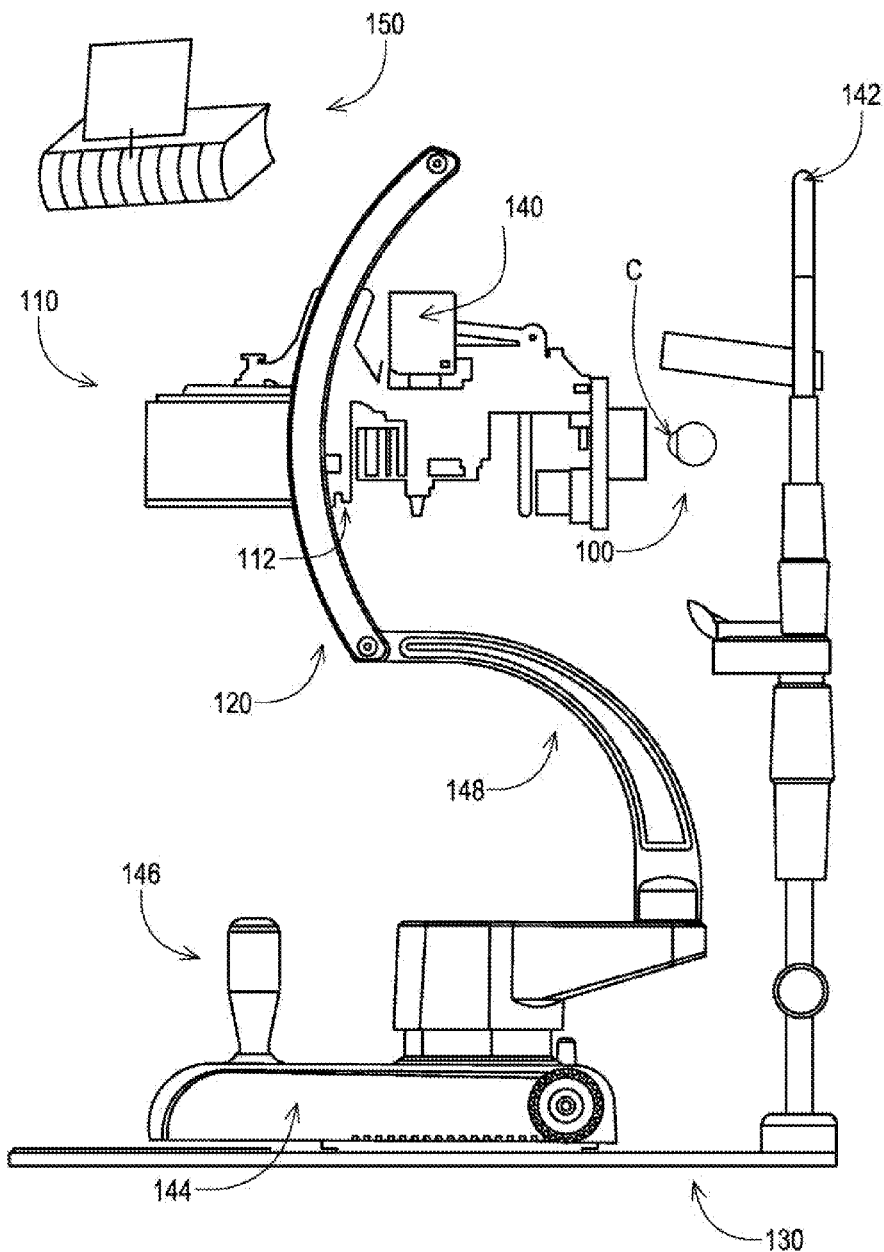
FIG. 1A illustrates a side perspective view of an apparatus for imaging an eye utilized in combination with a computer, in accordance with one embodiment of the present invention.

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

The apparatus for producing an image of an eye can be used for imaging the eye and other medical applications, including but not limited to anterior segment imaging of a eye including but not limited to the cornea, lens, an anterior chamber, a tear film, and also a posterior segment imaging including color fundus, fluorescein angiography, and ICG angiography imaging, as well as red-free, blue, red, near infrared, and infrared, spectral wavelengths of auto-fluorescence and functional imaging, such as flavoprotein autofluorescence, fluorophores in the retinoid cycle and others, curcumin fluorescence imaging, and other contrast agents used to image ocular and also neurodegenerative diseases. The apparatus for producing an image of an eye can be used with high magnification or can provide a very wide field of view and can be operated in a zoom mode. The apparatus for producing an image of an eye can be operated in a plenoptic mode allowing various focal lengths to be combined into a composite image that can be sectioned through, or combined into a single image.

One embodiment of the apparatus for producing an image of an eye allows for use in a stereopsis mode for nearly real-time generation of stereo images. The apparatus for producing an image of an eye can contain an eyecup to create a patient interface and darkened environment for operation in a non-mydriatic mode. The eyecup can be utilized to hold a person's eyelids open.

Another embodiment of the apparatus for producing an image of an eye can be utilized as a treatment targeting and/or treatment planning system.

The apparatus for producing an image of an eye is a low cost, hand-held and/or slit lamp mounted integrated and/or chinrest joystick assembly mounted, and/or microscope mounted eye imaging device suited for viewing a wide field and/or magnified views of retinal images through an undilated or dilated pupil.

The apparatus for producing an image of an eye is also capable of imaging the anterior segment of the eye as well, and sections and focal planes disposed between the sections. The apparatus for producing an image of an eye includes an illumination system, such as a LED, Halogen, Xenon, or other suitable illumination system, aperture stops and reflection masks. The illumination system includes one or more light sources, preferably white LED light or light of an individual wavelength for specific tests, or tunable light sources, that can be delivered into the optical system either along an optical axis or slightly off the optical axis from the center of the optical system or eye and return the imaging path from the retina.

The apparatus for producing an image of an eye provides entry of light rays into the eye for wide field retinal illumination, reduced glare and elimination of primary artifacts and reflections. Aperture stops, flipping masks, image processing, and/or off-axis illumination eliminates unwanted reflections or glare from being formed in the retinal image. The apparatus for producing an image of an eye is well suited for retinal viewing through an undilated pupil, such as a non-pharmacologically dilated pupil or a pupil dilated as small as 1.5 mms. and provides that the apertures and masks are sized in accordance with the diameter of an undilated pupil. The adjustment of this aperture and/or masks may be fixed or may be adjusted by the user. It also may automatically sense pupil size and self-optimize the size of the aperture and/or masks, and position of the light source, and masks. The apparatus for producing an image of an eye may utilize a reflection mask that momentarily blocks unwanted reflections while still leaving other areas of the image illuminated. Artifact-free regions from sequential images can also be combined to form a composite artifact-free image. The apparatus for producing an image or continuous movie of an eye may utilize a means of tracking the eye and adjusting to different views thereby moving artifacts to different geographic regions in the eye, and subsequently combining those images or sections of images into a final composite image that is artifact-free.

Another embodiment of the apparatus for producing an image of an eye utilizes one, two or more sources of illumination with a lateral shift and/or rotation of optical elements to shift the illumination and/or field of view, combined with fast sequential mask flipping. These optical designs also illuminate and provide an image with a wider field of view on the retina than current fundus cameras. Also, when images are combined, a final image with more uniformly distributed illumination, sharper focus and aberration correction is created.

The apparatus for producing an image of an eye contains an image processing algorithm that automatically detects any artifacts in the image and performs an image reconstruction that uses the valid image information from the corresponding image(s) where the artifact was masking the retina in the source image. The apparatus for producing an image of an eye may or may not utilize strobe lighting but does combine several images and blends the images together after performing similar artifact removal from one or more series of images, and/or changes in patient fixation.

The optical design may contain one or more light sources and may add a prism, such as a half penta prism, Schmidt prism or custom-made prism that redirects the illumination and imaging paths to be slightly offset from each other, creating overlapping illumination and images for an increased field of view, and also be utilized in combination with sequentially arranged flipping masks. These alternate illumination and imaging paths may enter the pupil in an angular way compared to the optical center or may enter slightly off axis but parallel to the center of the optical system. The angle of separation of these various overlapping light sources and imaging paths may be variable depending upon pupil size. These may adjust automatically based upon automated detection of pupil size.

Another embodiment of the apparatus for producing an image of an eye affords for tilting optical components to remove or specifically position reflections and artifacts. The apparatus for producing an image of an eye contains a manual focus and/or an autofocus mechanism. The apparatus for producing an image of an eye has an automatic exposure algorithm and image brightness and contrast optimization algorithm to optimize image quality. The apparatus for producing an image of an eye may contain an image stabilization or eye tracking algorithm. The apparatus for producing an image of an eye has an alignment mode in either visible, NIR, or IR light that allows the user to align an eye image along an external pupil and/or infrared or visible light image of the retina. The apparatus for producing an image of an eye may contain an alignment algorithm and mechanical or automated control for aligning a pupil of the eye along an optical axis to the patient's pupil.

The apparatus for producing an image of an eye may contain a spatial light modulator for positioning and shaping the illumination beam according to the sensed location and dimensions of the pupil, in combination with a flipping mask for artifact removal. The apparatus for producing an image of an eye may measure and record the pupil size. The apparatus for producing an image of an eye may record pupillary response to stimuli introduced into the optical train for purposes of perimetry testing. The apparatus for producing an image of an eye may contain a mode of dark adaptation testing that introduces a flash to bleach the retina followed by internal stimuli of various wavelengths to determine rod and/or cone response, especially in the tracking of age related macular degeneration or AMD and other disease states. The apparatus for producing an image of an eye may contain a mode of performing optical coherence tomography in combination with the other imaging modalities. The apparatus for producing an image of an eye may employ an infra-red or near infra-red filter or light source that is in place for alignment mode and flipped out to allow other spectral wavelengths to pass and subsequent image capture.

One embodiment of the apparatus for producing an image of an eye uses an anti-shake optical, eye tracking, and/or other image stabilization software algorithm to automatically align the apparatus for producing an image of an eye to the patient's eye and also eases alignment of images for averaging and other image processing and viewing functions.

Another embodiment of the apparatus for producing an image of an eye that achieves optical artifact shifting via an oscillating objective lens or other internal optical or masking element that achieves producing an image located adjacent to the artifact produced by the oscillating objective lens. Real-time artifact remapping may be applied to this set of images for artifact elimination. This embodiment of the apparatus for producing an image of an eye affords for the creation of real-time stereo pairs of images due to oscillation and shifting. Oscillation could be of various frequencies to achieve a desired result. This may also be combined with eye tracking and changes in patient fixation in order to create a wide field view of the retina generated from several images, movies, or sections of images either in post-processing or near real-time.

Another embodiment of the apparatus for producing an image of an eye builds a comprehensive image through multiple planes of the eye by stepped focus and the introduction of additional optical elements to achieve focus shift.

Another embodiment of the apparatus for producing an image of an eye utilizes all previously described modalities incorporated into a therapeutic planning and/or targeting system.

Fast sequential flipping of an artifact mask and subsequent image reconstruction can be achieved with a variety of illumination strategies aside from the point source illumination described. The mask can be implemented by utilizing a mechanical flipping element, a shuttered opto-electronic window mechanism, or a rotating mask synchronized with an image capturing capability from one or more light sources. The area underneath the artifact would be temporarily exposed and captured, and subsequently combined with other areas of previously acquired images for creation of a composite artifact-free image. The mask could also serve as a patient fixation and/or eye alignment device or mechanism.

The apparatus for producing an image of an eye could contain a wireless SD card or other embedded wireless device for automatically transmitting images to a host computer or other storage device or software. The apparatus for producing an image of an eye could allow the user to take an image of the patient's name, apply optical character recognition technology, detect the patient's first name, last name and chart code, record the date and time of the image and automatically store the information in a database and wirelessly transmit the information to a host. This could be performed by an embedded processor in the apparatus for producing an image of an eye or by a host computer.

The apparatus for producing an image of an eye may also utilize a flexible eyecup that could be fixed to the apparatus for producing an image of an eye, or be utilized as a disposable flexible eyecup that attaches to the end of the apparatus for producing an image of an eye for use on each patient. The eyecup could be made of baffled flexible material such as rubber, plastic, or any type of suitable material that gently surrounds the patient's eye to create a darkened environment and could also be used to hold a patient's eyelids open. The eyecup could have an angular spring internal mechanism (or sponge-like compressible material) that holds the patient's eyelids open. The baffles are flexible to allow for adjustable and proper positioning around the patient's eye.

One embodiment of the apparatus for producing an image of an eye contains a firm rubber or plastic portion of the eyecup that is located approximately along a vertical axis to the eyecup that is used to hold a patient's upper eyelid open during imaging. The rest of the eyecup is placed over the patient's eye to create a darkened environment. This mode of operation creates a darkened environment for natural pupil dilation for the patient. Another embodiment of the eye cup is only the upper most portions used to hold the upper eye lid open during imaging.

The apparatus for producing an image of an eye could also include an infrared or near-infrared LED light or other light source illumination system, coupled with a detector, such as a charge coupled device or CCD, a complementary metal oxide semiconductor or CMOS, or other suitable type of detector that is sensitive to light at a particular wavelength. The detector would be used for alignment, but could also be turned off and the patient would be flashed with visible light, green light, blue light or red-free light wavelengths for imaging including fluorescein angiography, ICG angiography, fundus auto fluorescence, hyper and multi-spectral imaging, curcumin fluorescence imaging or other wavelengths used in other auto fluorescence or functional imaging with a variety of contrast agents.

The apparatus for producing an image of an eye could have all of the previously described embodiments in addition to creating a multi-focal plenoptic image or other image or movie that is created from images at multiple focal planes. This image is formed by a camera system that has micro-lenses over the top of a CCD or CMOS pixel array that is divided into two or more focal planes. This image would be calibrated and reconstructed into a multi-focal plenoptic image. Alternatively, a plenoptic multifocal image could be created by using a manual or auto-focus mechanism that finds optimal center focus and then acquires additional images with slight focus adjustments bracketed around the center focal point. These images could then be combined into a single plenoptic image or could be combined into an interactive movie image that allows the user to scroll through multiple focal planes. The algorithm to combine images would automatically align the images correcting for translation, rotation, curvature, and magnification differences between the images. The software would detect high frequency information in each image plane corresponding to an element. The plenoptic algorithm could also be used for combining images of different modalities. For example, ICG images highlighting choroidal detail could be combined with fluorescein images highlighting retinal detail. The plenoptic algorithm could be used for any combination of retinal images. The plenoptic algorithm could also be applied to images from multiple focal planes in the anterior segment of the eye. These modalities could also be combined with OCT data sets for sectioned retinal images that contain multiple image planes and sections.

One embodiment would allow for a continuous capture of images or movies through the entire eye from the anterior portion to the posterior portion and allow for application of the plenoptic algorithm to form a single plenoptic image or movie loop viewing function.

Another embodiment of the apparatus for producing an image of an eye allows for simultaneous or fast sequential capture of multiple imaging modalities and recombination into composite images as single frames or averaged images.

Another embodiment of the apparatus for producing an image of an eye could also be implemented in combination with a wave front sensor for automated positioning and correction of aberrations. The apparatus for producing an image of an eye could be combined with a deformable mirror and wave front sensor for correction of both low and high order aberrations. The apparatus for producing an image of an eye and all its embodiments could include components, light sources and filters that allow all retinal types of retinal imaging including but not limited to color fundus imaging, red-free, ICG angiography, fluorescein angiography, IR or near IR imaging, all forms of fundus auto fluorescence at various wavelengths, hyper and multi-spectral imaging, curcumin fluorescence imaging, and functional imaging with a variety of contrast agents.

Another embodiment of the apparatus for producing an image of an eye would utilize elements of the imaging portions of the slit lamp and be rotated in front of a slit lamp objective lens of the slit lamp.

Another embodiment of the apparatus for producing an image of an eye would utilize modification of the slit lamp that also utilizes the slit lamp's existing illumination system for retinal and anterior segment imaging.

Another embodiment of the apparatus for producing an image of an eye would be for handheld use, integrated with a direct or indirect ophthalmoscope, or having the apparatus for producing an image of an eye connected to a microscope.

Another embodiment of the apparatus for producing an image of an eye would be to combine the apparatus for producing an image of an eye with optical coherence tomography or OCT test modality.

Another embodiment of the apparatus for producing an image of an eye utilizes a mode where images are captured and move together in real time, real time movie streams are analyzed for artifacts and optimal focus, and images are reconstructed from "good" sections of images taken from the movie stream.

Another embodiment of the apparatus for producing an image of an eye allows the user to program an internal fixation target for the patient to follow and then attach images together as they are captured. This would also be applied for artifact removal. Multiple images could be stored as a movie file, single frames or a single frame attached together. The internal fixation could be in a variety of forms including a flipping "stick" that contain an LED array that can be programmed by the user to a specific position. The internal flipping LED stick is automatically flipped out of place during image capture.

Another embodiment of the apparatus for producing an image of an eye introduces stimuli via a LCD light and a beam slitter or other suitable mechanism for microperimetry testing.

Another embodiment of the apparatus for producing an image of an eye utilizes interchangeable objective lenses for different fields of view and also for anterior segment imaging.

Another embodiment of the apparatus for producing an image of an eye include lens, stops and a masking device that is optimized for retro-illumination imaging of the eye lens.

Another embodiment of the apparatus for producing an image of an eye applies a dark-correction algorithm whereby an image of the CCD or CMOS chip is captured in a darkened environment and is processed, stored and deleted from captured images to reduce noise and improve overall image quality.

Another embodiment of the apparatus for producing an image of an eye allows utilization in a switchable normal focus or plenoptic mode to allow for capture of images from multiple focal planes.

Another embodiment of the apparatus for producing an image of an eye utilizes a stereo optical system for real time stereoscopic viewing. This is achieved in a variety of different ways including optical shift, CCD lens overlay or micro lens overlay and can be derived from video scanning, motion and/or focus cameras, multiple cameras, or multi-chip cameras.

Another embodiment of the apparatus for producing an image of an eye would have dual stereo cameras (or dual chips/optics in a single camera). This can be mounted in the slit lamp through beam-splitter or oculars of a traditional slit lamp beam splitter.

Another embodiment of the apparatus for producing an image of an eye involves an alternative to a rapid alternate strobing of an LED light that would instead utilize a rotating optic mask at a rapid pace that is synchronized with a video input. This would result in multiple images for artifact-free reconstruction.

Another embodiment of the apparatus for producing an image of an eye utilizes a rotating light source that can also be utilized in combination with other previously mentioned features. This can be done with several optical elements in the apparatus for producing an image of an eye including a rapidly rotating synchronized optic like a wedge prism. The artifact would be mapped to the other image to remove the artifact. The mapping could be done with image processing or with calibration and real-time memory mapping. The mapping also serves as a means of increasing the field of view of the image and could be put together in a panorama as a single image.

Another embodiment of the apparatus for producing an image of an eye uses any or all of the described elements and produces a panorama together in real time from the video stream. This could also be obtained by a random or automated pre-programmed change in patient fixation. This could also be achieved via a programmable swing and/or tilt of the device to change position and image view.

FIG. 1A illustrates an exploded perspective view of an apparatus for producing an image of an eye 100, in accordance with one embodiment of the present invention. The apparatus for producing an image of an eye 100 includes a video camera 110, video camera optics 112, a camera housing 120 mounted on a slit lamp chinrest and joystick assembly 130 and illumination source optics 140. The video camera 110 is a digital camera but can be any type of suitable camera for use with the apparatus for producing an image of an eye 100. The slit lamp chinrest and joystick assembly 130 includes a head support 142, a movable base 144, a joystick 146, and a housing support 148. The head support 142 holds the patient's chin and forehead in a known, fixed position. The head support 142 is provided with elevation adjustments to provide a comfortable resting place for the patient's head. The position of the camera housing 120 relative to the head support 142 can be adjusted in both relative gross and fine increments using the joystick 146. The apparatus for producing an image of an eye 100 is used in combination with a computer system 150, which is described in greater detail in FIG. 1D. The computer system 150 can be any suitable computer system 150 that can be used in combination with the apparatus for imaging an eye 100.

The personal computer 150 forms the center of the apparatus for imaging an eye 100, processing data and controlling the operation of other components of the apparatus for imaging an eye 100. Connected to the personal computer 150 is a video camera 110. An observation video monitor which can be the screen of the personal computer, a slit lamp chinrest and joystick assembly 130, illumination source optics 140, and video camera optics 112 are associated with the camera housing 120.

The personal computer 150 is preferably a relatively compact computer, embedded computer, or tablet computer of relatively high processing power using a standardized operating system and having standardized card slots for interfacing peripheral equipment such as memory cards, video board, printer and a monitor. The personal computer 150 will run customized software as will be described in detail later. The monitor or screen of the personal computer will have very-high-resolution color graphics capability appropriate for displaying images under analysis.

The digitizing board accepts a digital file or video input from video camera 110 and functions as a "frame grabber,"

or display. That is, when activated by a signal from the personal computer 150, the digitizing board will collect video and/or digital data and images from video camera 110 at that instant and store into digital data. The digital data produced is stored in memory and made available to personal computer 150 for analysis.

Figure 1B:
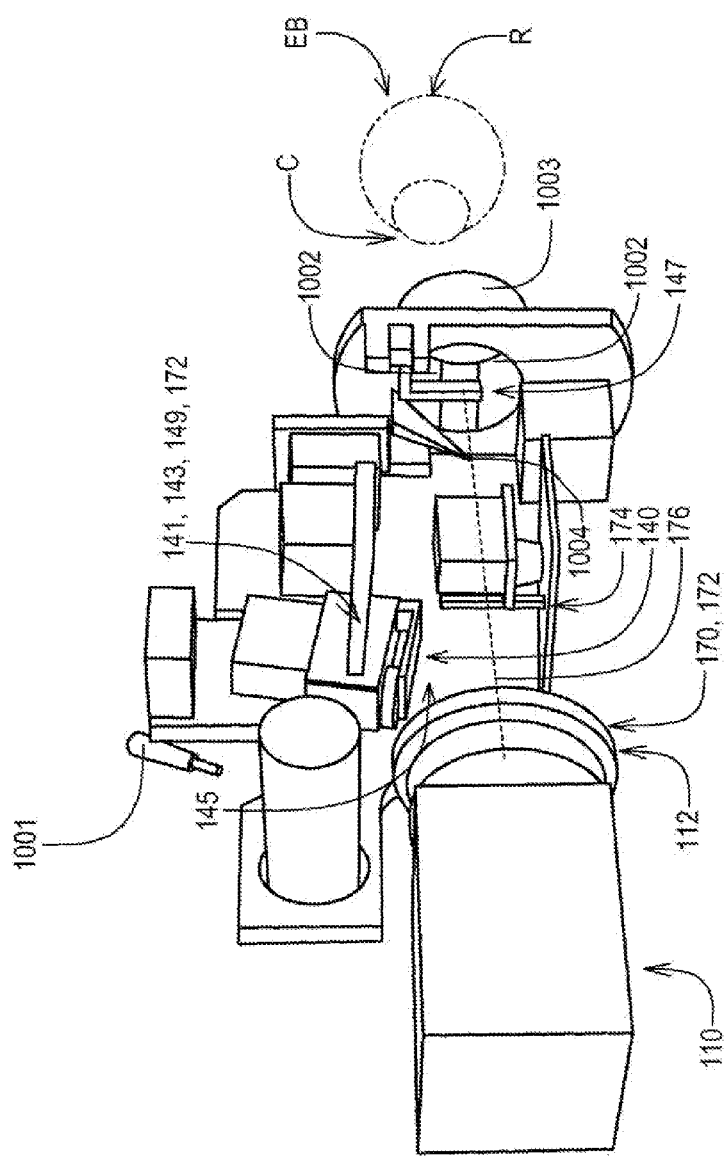
FIG. 1B illustrates a side perspective view of a camera housing, in accordance with one embodiment of the present invention.

FIG. 1B illustrates a side perspective view of a camera housing 120 of the chinrest and joystick assembly 130, in accordance with one embodiment of the present invention. The camera housing 120 containing the video camera 110 illumination source(s) and optics 140 is proximate to a sectioned patient eyeball EB with a cornea C and a retina R. Housing 120 may be cylindrical or of any other suitable shape. The housing 120 has no forward protruding parts, which prevents accidental direct contact of any part of the apparatus for imaging an eye 100 with the patient's cornea C or facial features during movement of the housing 120 relative to the patient's eyes. This is advantageous since there is no contact with the patient's cornea C to accomplish examination and image capture. The external housing 120 and the optics have been designed to maintain some distance to the cornea C, increasing patient comfort while any testing is being performed. A flexible interface such as a rubber cup 180 can be provided at the interface between the housing 120 and the patient's eyeball EB.

The inclusion of illumination source optics 140, camera optics 112 and the video camera 110 in the camera housing 120 provides a high degree of accessibility. By placing all elements of the apparatus for imaging an eye 100 in one camera housing 120, allows for an affordable design. Additionally, the relatively small design of the apparatus for imaging an eye 100 compared to that of a fundus camera for observation and image capture provides for a shorter and more efficient optical pathway. The compact design and simplicity of optics 112,140 reduces production costs and permits greater ease of use by the operator. The design of the apparatus for imaging an eye 100 allows imaging through a smaller pupil as compared to a fundus camera.

Video camera 110 is relatively compact and incorporates a color or monochrome CCD, CMOS, or multi/hyper-spectral image sensor. The focus of the patient may also be achieved by focus of internal optical elements of the digital camera. Lens contained inside camera 100 may be focused automatically or manually by observing the image displayed on an observation video monitor. Alternatively, an electronic auto-focusing control system could be provided for automatically adjusting the focus of lens inside camera 100. The video camera 110 can also contain a monochrome or color CCD or CMOS sensor (not shown).

The observation optics 112 associated with the video camera 110 include the lens 170, an observation aperture 172, and a filter 174. The observation aperture 172 and the filter 174 transmit light reflected from the retina R to the lens 170 and to the video camera 110. The filter 174 is an infrared stepping filter (or other filter for other imaging procedures) which improves the contrast of the image seen by the video camera 110.

Indo-cyanine green angiography, color fundus photography, auto-fluorescence, or fluorescein angiography, curcumin fluorescence imaging, or other filter sets may be utilized by the apparatus for imaging an eye 100. These filters will be mounted so as to be selectively rotatable in and out of the view axis of the video camera 110 according to the function being performed. The rotation may be accomplished manually or under computer servo control.

The projection optics 140 of the invention projects light onto the retina R, off axis at an angle to the central axis 176 of lens 170 of video camera 110. The projection optics 140 includes a lamp 141, a lamp lens group 143, a mirror 145, and a projection aperture 172. A control 1001 is provided to adjust the intensity and position of the lamp 141, either manually or under the control of the computer system 150. The control is also used to sequentially control multiple lamps 141, shifting optical elements, and flipping masks 147, LED flipping internal fixation pointer 1004, and image capture trigger.

The light from lamp 141 passes through aperture 149 and the series of lamp lens group 143 that typically has two lenses. The lenses of lamp lens group 143 concentrate the light output of lamp 141. Lamp lens group 143 may preferably consist of multiple lenses or a single aspheric lens. The light is then deflected by mirror 145 which is placed at a critical pitch angle relative to the video camera 110 and the projection optics 112. The light passes from the mirror 145 past the flipping mask 147 which concentrates the light. The light then passes through a plurality of small pupil masks 1002. The light then passes through the objective lens 1003. The light then passes past the cornea C and is projected onto retina R.

All the masks and apertures used, such as flipping mask 147 and aperture 149 and 1002, are appropriately sized apertures. Although the lamp 141 has been described as a generalized LED lamp, it should be noted that the lamp 141 can be any source of radiant energy. In one preferred embodiment, the lamp 141 is an infrared illumination source, and the specifications of filter 174 are adjusted accordingly to pass the wavelength of the lamp 141. Infrared illumination may be particularly desirable for alignment prior to acquiring images without the problems generated by lack of pupil dilation. The image can be captured in a relatively dark room using infrared illumination, so that the eye being imaged is naturally dilated. There is also a means for sequentially turning the light source on and off in synchronization with image capture under each condition, which is a computer system 150, further described in FIG. 1C.

In another preferred embodiment which addresses the problems caused by lack of pupil dilation during imaging, the lamp 141 may be strobed in full color, red free, NIR or other preferred wavelength (based on imaging procedure desired) during image acquisition rather than being kept on constantly, thereby preventing the energy of lamp 141 from narrowing the pupil prior to image capture. Because of the unique design of the projection optics 140 and the capabilities of the image processing and analysis software employed, useful image data from each image can be collected with minimum pupil dilation. Specifically, the pupils of the eye being imaged may have a diameter of as little as 2 mms. The projection optics 140 projects light onto the retina R off axis from the observation path of video camera 110. Another preferred embodiment places an adjustable mask 1002 adjacent to objective lens 1003 that adjust to the patient's pupil to optimize the image when the pupil is small.

Figure 1C:
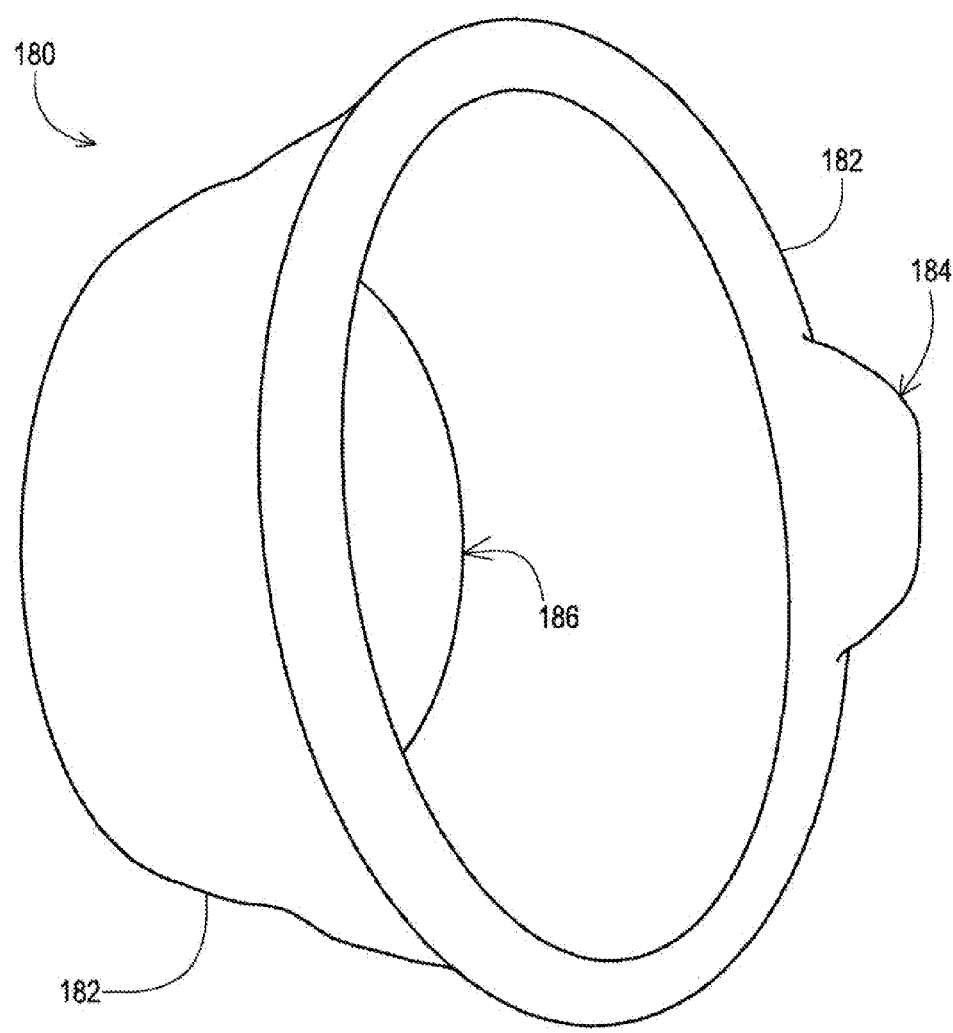
FIG. 1C illustrates a front overhead perspective view of an eyecup, in accordance with one embodiment of the present invention.

FIG. 1C illustrates a front overhead perspective view of an eyecup 180, in accordance with one embodiment of the present invention. The eyecup 180 protrudes outward from the perimeter 182 at an approximate 10% increase at the approximate 0° 184 and 180° degree 186 positions on the perimeter 182. Further details regarding the eyecup 180 are described in FIG. 3 and its description.

Figure 1D:
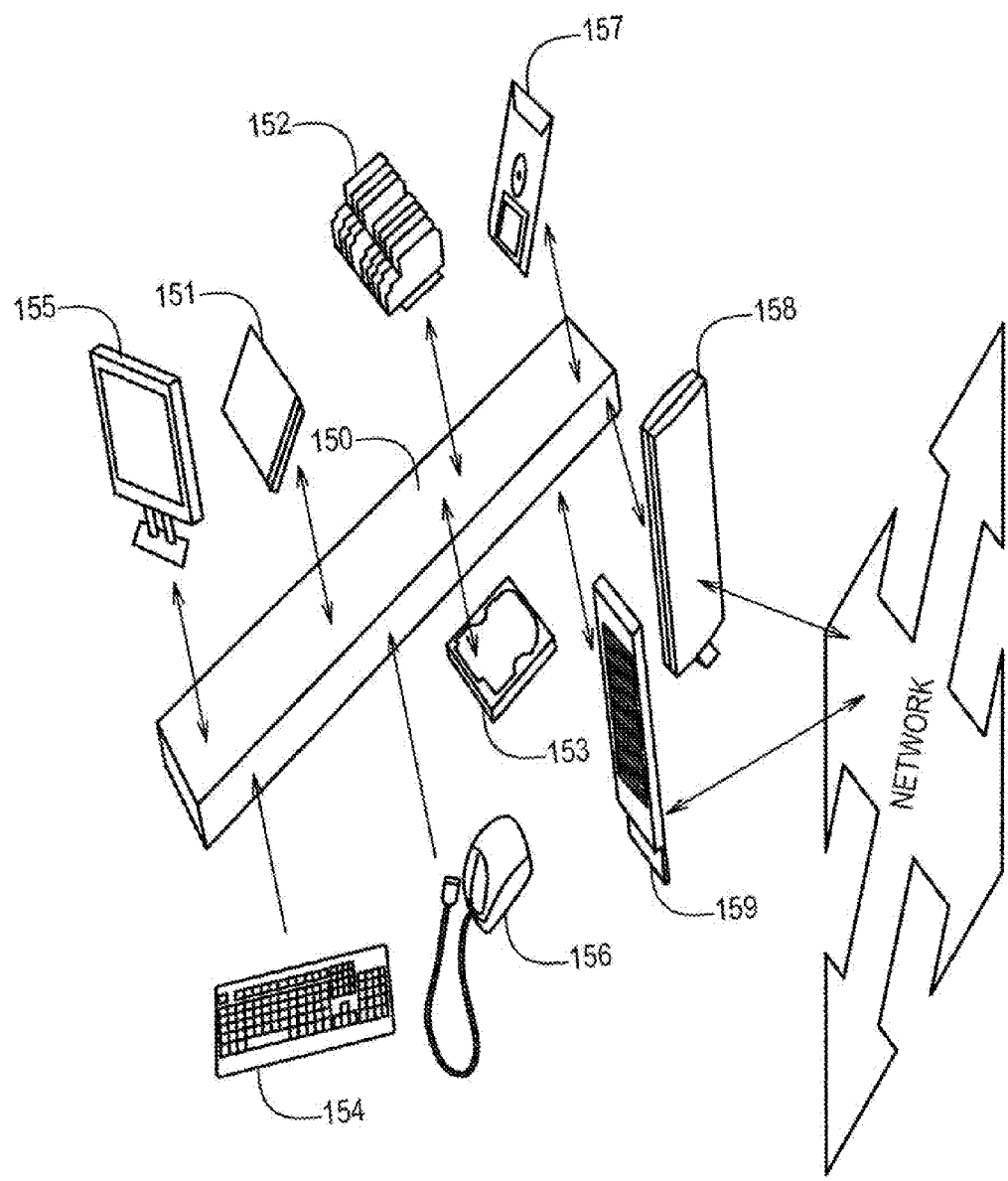
FIG. 1D is an exploded diagonal side perspective diagram of a computer system, in accordance with one embodiment of the present invention.

FIG. 1D is an exploded diagonal side perspective diagram of a computer system 150, in accordance with one embodiment of the present invention. Such a computer system 150 includes a processing unit such as a CPU 151 connected by a bus to a random access memory or RAM 152, a storage device 153, a keyboard 154, a display 155 and a mouse 156. In addition, there is software 157 for entry of data embodying the apparatus for imaging an eye 100. An example of a computer system 150 can be a Dell personal computer operating on the Microsoft Windows operating system, or Linux, Macintosh, etc. The invention can also be used on a laptop computer, cell phone, PDA, Apple™ Mac™, tablet, or other computerized device. The computerized system 150 can also be used in combination with a wireless modem 158 or network interface card 159.

The various method embodiments of the invention will be generally implemented by a computer executing a sequence of program instructions for carrying out the steps of the method, assuming all required data for processing is accessible to the computer. The sequence of program instructions may be embodied in a computer program product comprising media storing the program instructions. As will be readily apparent to those skilled in the art, the present invention can be realized in hardware, software, or a combination of hardware and software. Any kind of computer/server system(s)—or other apparatus adapted for carrying out the methods described herein—is suited. A typical combination of hardware and software could be a general-purpose computer system with a computer program that, when loaded and executed, carries out the method, and variations on the method as described herein.

Figure 2:
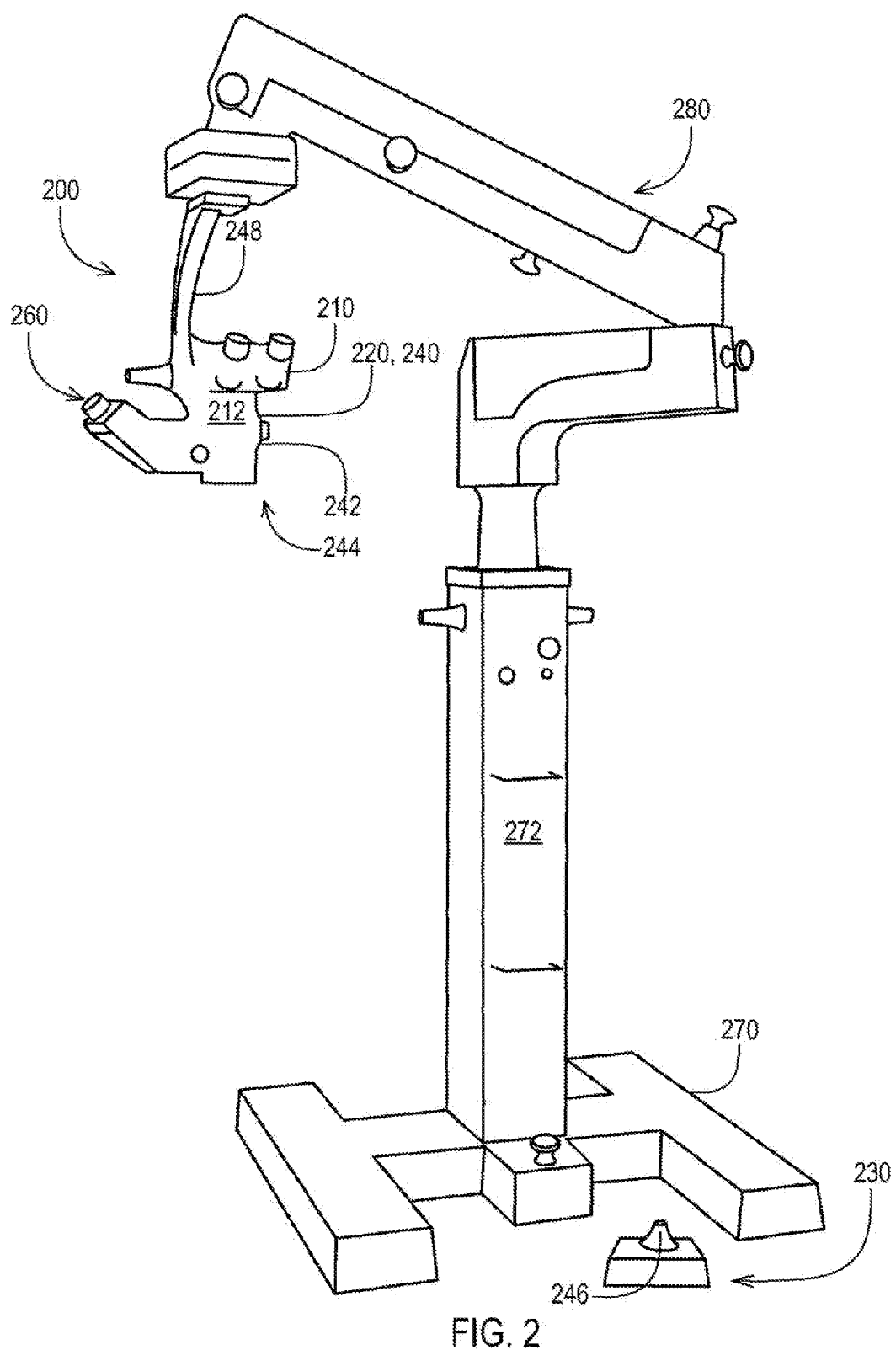
FIG. 2 illustrates a side perspective view of an apparatus for imaging an eye utilized in combination with a microscope, in accordance with one embodiment of the present invention.

FIG. 2 illustrates a side perspective view of an apparatus for imaging an eye 200 utilized in combination with a microscope 260, in accordance with one embodiment of the present invention. FIG. 2 illustrates a side perspective view of an apparatus for imaging an eye 100 that has all of the same components of the apparatus for imaging an eye 100 described in FIG. 1A, except the microscope 260 and the computer system 150. The apparatus for producing an image of an eye 200 includes a video camera 210, video camera optics 212, a camera housing 220 mounted on a patient alignment assembly 230 and illumination source optics 240. The microscope assembly 230 includes a support 242, a movable base 244, and housing support 248. The position of the camera housing 220 relative to the head support 242 can be adjusted in both gross and fine increments using the joystick 246. The microscope 260 can be any suitable microscope that can be used in combination with the apparatus for imaging an eye 200.

Figure 3:
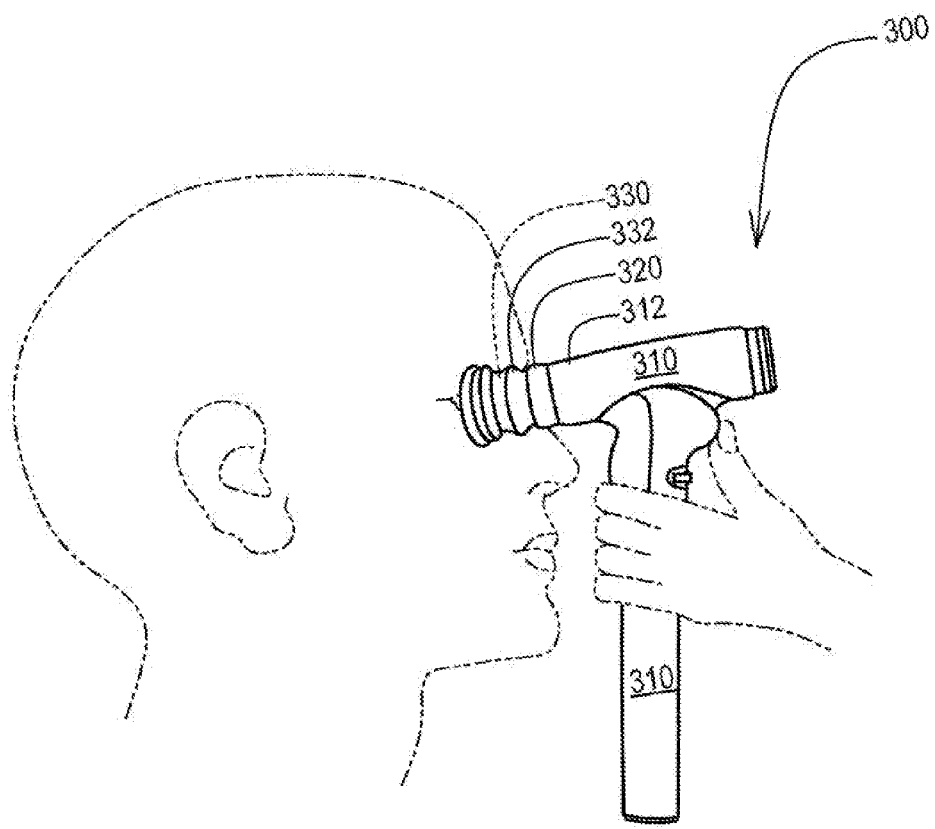
FIG. 3 illustrates a side perspective view of an apparatus for imaging an eye that is hand-held, in accordance with one embodiment of the present invention.

FIG. 3 illustrates a side perspective view of a hand held apparatus for imaging an eye 300, in accordance with one embodiment of the present invention. The hand held apparatus for imaging an eye 300 includes all of the same components of the apparatus for imaging an eye 100 described in FIG. 1B and can be used in combination with a microscope 260 (FIG. 2) or a computer system 150 (FIG. 1A). The hand held apparatus for imaging an eye 300 utilizes a hand-held housing 310 instead of a camera housing 120 as described in FIGS. 1A and 1B, but utilizes all of the same optical and electrical components disposed within the hand-held housing 310.

The hand-held apparatus for producing an image of an eye 300 may also utilize a flexible eyecup 320 that could be fixed to the hand-held apparatus for producing an image of an eye 300, or be utilized as a disposable flexible eyecup that attaches to the end 312 of the apparatus for producing an image of an eye for use on each patient. The flexible eyecup 320 could be made of baffled flexible material 322 such as rubber, plastic, or any type of suitable material that gently surrounds the patient's eye to create a darkened environment and could also be used to hold a patient's eyelids open. The flexible eyecup 320 could have an angular spring internal mechanism 330 that holds the patient's eyelids open. The baffles 322 are flexible to allow for adjustable and proper positioning around the patient's eye.

Figure 4A:
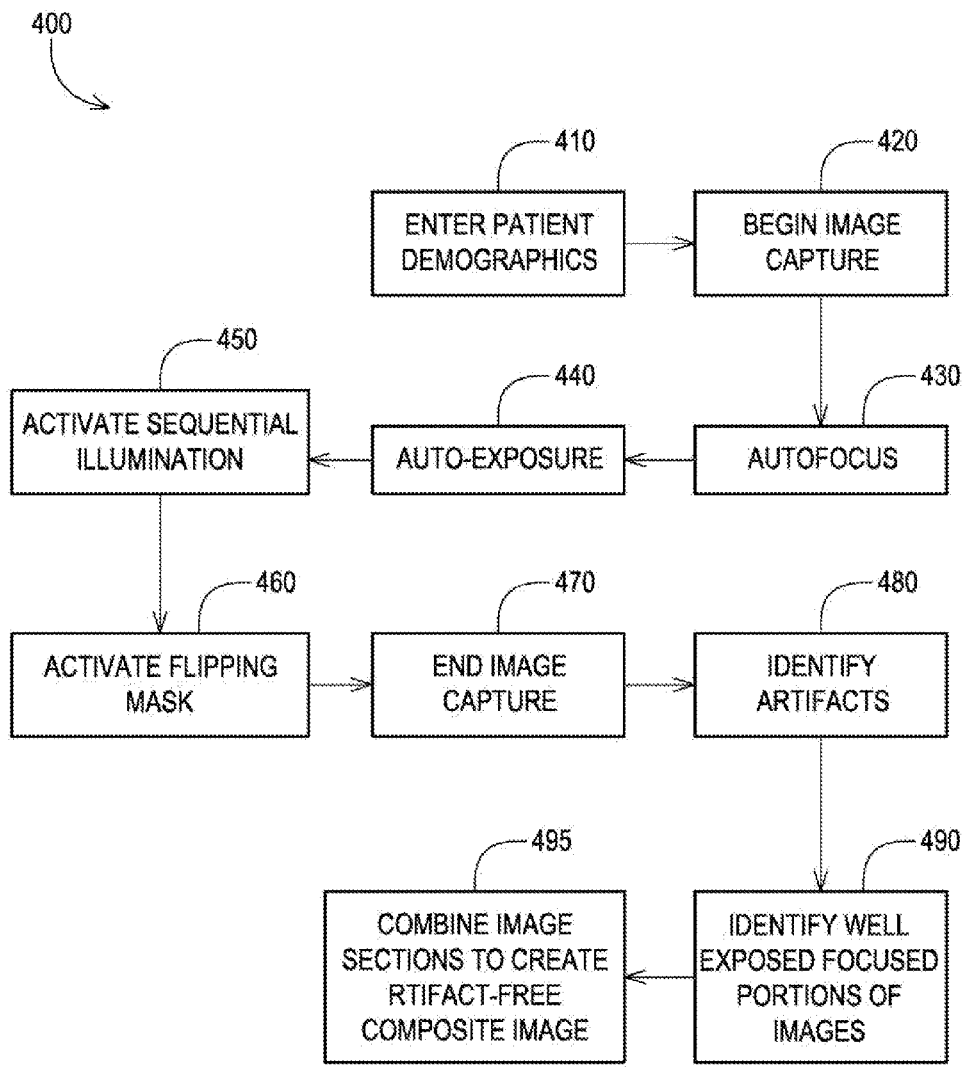
FIG. 4A is a flowchart of a method for producing an image of an eye, in accordance with one embodiment of the present invention.

FIG. 4A is a flowchart of a method for producing an image of an eye 400, in accordance with one embodiment of the present invention. The overall method 400 illustrates the architecture, functionality, and operation of possible implementations of systems, methods and computer program products according to various embodiments of the present invention. In this regard, each step in the method may represent a module, segment, or portion of code, which comprises one or more executable instructions for implementing the specified logical function(s). It should also be noted that, in some alternative implementations, the functions noted in the step may occur out of the order. For example, two steps shown in succession may, in fact be executed substantially concurrently, or the steps may sometimes be executed in the reverse order, depending upon the functionality involved. It will also be noted that each step of the overall method, and combinations of steps in the overall method, can be implemented by special purpose hardware-based systems that perform the specified functions or acts, or combinations of special purpose hardware and computer instructions.

The overall method may be embodied as a system, method, or computer program product. Accordingly, the overall method may take the form of a hardware embodiment, a software embodiment, or an embodiment combining software and hardware. Furthermore, the overall method may take the form of a computer program product embodied in any tangible medium of expression having computer-usable program code embodied in the medium.

Any combination of one or more computer usable or computer readable medium(s) may be utilized. Specific examples of the computer-readable medium can include a hard disk, a random access memory (RAM), a read-only memory (ROM), an erasable programmable read-only memory (EPROM), or flash memory or a portable compact disc read-only memory (CD-ROM). In the context of this document, a computer-usable or computer-readable medium may be any medium that can be used by or in connection with the instruction execution system or apparatus. Computer program code for carrying out operations of the overall method may be written in any combination of one or more programming languages. The program code may execute entirely on the user's computer, partly on the user's computer, as a stand-alone software package, partly on the user's computer and partly on a remote computer or entirely on the remote computer or server.

The overall method is described above with reference to a computer program according to an embodiment of the invention. It will be understood that each step, and combinations of steps shown, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the method.

These computer program instructions may also be stored in a computer-readable medium that can direct a computer or other programmable data processing apparatus to function in a particular manner, such that the instructions stored in the computer readable medium produce an article of manufacture including instructions means which implement the function specified in the steps.

The computer program instruction may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions specified.

In the first step 410, the patient's demographics are entered. The patient places his or her head in the slit lamp chinrest and joystick assembly so that the patient's head is held substantially immobile. The operator adjusts the position of housing adjustments on the chinrest and joystick assembly and particularly using the joystick until the projection optics and the video camera are aimed through one or the other of the patient's corneas of the eye. The image capture is begun 420 and is triggered by the operator or automatically by the computer based on an algorithm for optimal image alignment by the operator pressing a button on the joystick, Bluetooth keypad, tablet computer, or triggering a foot pedal to signal the apparatus that the image of video camera should be recorded. Then an autofocus procedure and auto-exposure procedure 430, 440 are executed to obtain a clear image of the patient's retina. Illumination is then activated 450 and then either the optical shift activated 460, or the flipping mask 147 (from FIG. 1B) is actuated (depending upon configuration).

Figure 4B:
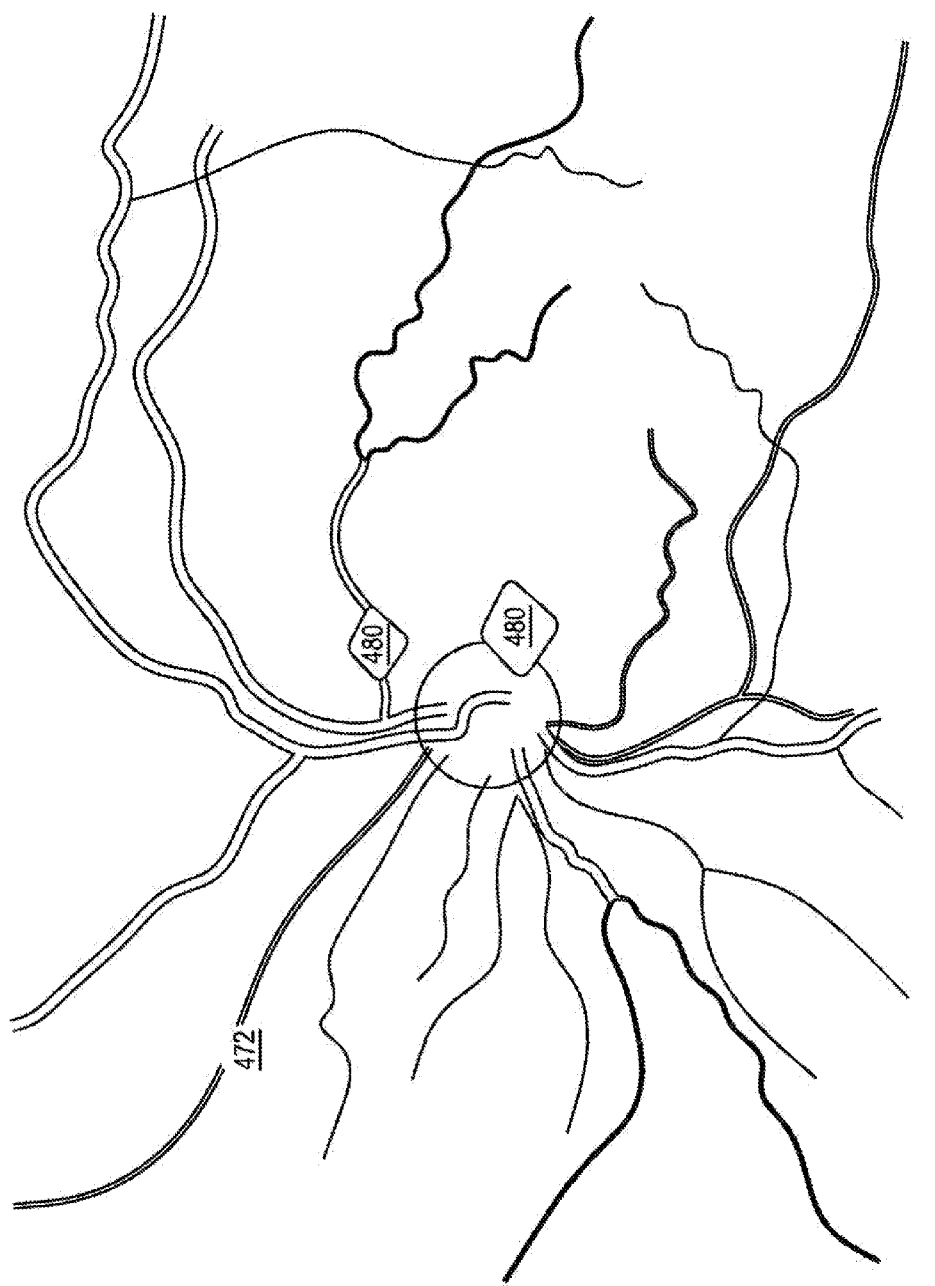
FIG. 4B illustrates a front perspective view of an eye image capture and artifact dots, in accordance with one embodiment of the present invention.

FIG. 4B illustrates a front perspective view of an eye image capture 472 and artifact dots 480, in accordance with one embodiment of the present invention. Subsequently the image capture is ended 470 and artifacts are identified 480.

Figure 4D:
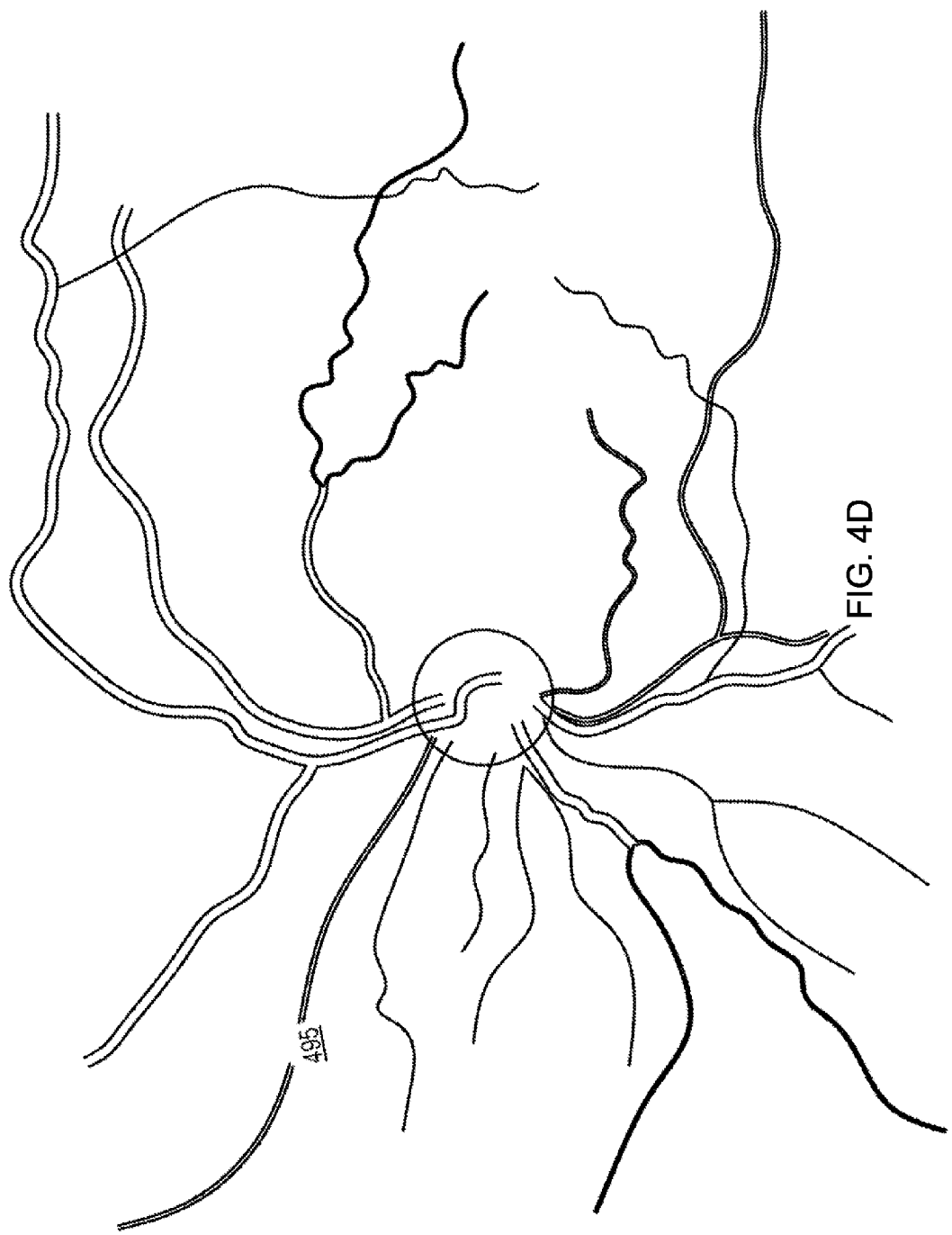
FIG. 4D illustrates a front perspective view of artifact-free composite eye image, in accordance with one embodiment of the present invention.

FIG. 4C illustrates a front perspective view of a flipping mask 485 on an eye image capture 490, in accordance with one embodiment of the present invention. After identifying artifacts the flipping mask 147 is identified additionally well exposed focused portions of each image are identified 490 and image sections are combined to create an artifact-free composite image 495. FIG. 4D illustrates a front perspective view of the artifact-free composite eye image 495, in accordance with one embodiment of the present invention. The artifact-free composite image 495 is previously described in FIG. 4C.

In response to the indication of the operator (or via controller) the image should be recorded, the personal computer will cause the image(s) of video camera to store digital data representing the captured image(s). The overall method 400 can also be used in combination with a microscope. The overall method can be used with scanning the device via swing or tilt mechanism or patient fixation.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

The invention claimed is:

1. A method for producing an image of a posterior and an anterior segment of an eye in combination with an image producing apparatus, comprising the steps of:
    entering patient demographics;
    beginning image or movie capture;
    optimizing masks and illumination position to pupil size;
    executing autofocus or intentional focus shift for plenoptic image;
    executing auto-exposure;
    activating sequential illumination;
    activating optical shift;
    activating mask flip;
    ending image or movie capture;
    identifying artifacts, masks and clear portions of images; and
    combining said images sections to create an artifact-free composite, plenoptic, averaged, stereo image or movie.

2. The method according to claim 1, wherein said apparatus is a hand-held apparatus either as a standalone device or incorporated with an existing direct or an indirect ophthalmoscope.

3. The method according to claim 1, wherein said apparatus is used in combination with a microscope, a slit lamp, an OCT, a microscope, a direct or indirect ophthalmoscope, a microperimetry device, or an existing fundus camera.

4. The method according to claim 1, wherein said apparatus is used in detecting amyloid in said retina.

5. The method according to claim 4, wherein said apparatus is used in said detecting of amyloid in said retina utilizing light sources, filters, spectrometer and sensors that allow curcumin fluorescence imaging, auto fluorescence imaging, hyper-spectral imaging, multi-spectral imaging, or OCT and subsequent image segmentation to identify amyloid associated with either ocular or brain conditions.

6. A method for producing an image of a posterior and an anterior segment of an undilated eye in combination with an image producing apparatus, comprising the steps of:
    entering patient demographics;
    beginning image or movie capture;
    optimizing masks and illumination position to pupil size;
    executing autofocus, or intentional focus shift for plenoptic image;
    executing auto-exposure;
    activating sequential illumination;
    activating optical shift;
    activating mask flip;
    ending image or movie capture;
    identifying artifacts, masks and clear portions of images;
    identifying well focused and well illuminated portions of said images: and
    combining said image sections to create an artifact-free composite, plenoptic, averaged, stereo image or movie.

7. The method according to claim 6, wherein said apparatus is a hand-held apparatus either as a standalone device or incorporated with an existing direct or an indirect ophthalmoscope.

8. The method according to claim 6, wherein said apparatus is used in combination with a microscope, a slit lamp, an OCT, a microscope, a direct or indirect ophthalmoscope, a microperimetry device, or an existing fundus camera.

9. The method according to claim 6, wherein said apparatus is used in detecting amyloid in said retina.

10. The method according to claim 9, wherein said apparatus is used in said detecting of amyloid in said retina utilizing light sources, filters, spectrometer and sensors that allow curcumin fluorescence imaging, auto fluorescence imaging, hyper spectral imaging, multi-spectral imaging, or OCT and subsequent image segmentation to identify amyloid associated with either ocular or brain conditions.

11. A non-transitory computer readable storage medium to produce an image of a posterior and an anterior segment of an undilated eye in combination with an image producing apparatus, comprising the steps of:

entering patient demographics;
beginning image or movie capture;
optimizing masks and illumination position to pupil size;
executing autofocus, or intentional focus shift for plenoptic image;
executing auto-exposure;
activating sequential illumination;
activating optical shift;
activating mask flip;
ending image or movie capture;
identifying artifacts, masks and clear portions of images;
identifying well focused and well illuminated portions of said images: and
combining said image sections to create an artifact-free composite, plenoptic, averaged, stereo image or movie.

12. The non-transitory computer readable storage medium according to claim 11, wherein said apparatus is a hand-held apparatus either as a standalone device or incorporated with an existing direct or an indirect ophthalmoscope.

13. The non-transitory computer readable storage medium according to claim 11, wherein said apparatus is used in combination with a microscope, a slit lamp, an OCT, a microscope, a direct or indirect ophthalmoscope, a microperimetry device, or an existing fundus camera.

14. The non-transitory computer readable storage medium according to claim 11, wherein said apparatus is used in detecting amyloid in said retina.

15. The non-transitory computer readable storage medium according to claim 14, wherein said apparatus is used in said detecting of amyloid in said retina utilizing light sources, filters, spectrometer and sensors that allow curcumin fluorescence enlarging, auto fluorescence imaging, hyper spectral imaging, multispectral imaging, or OCT and subsequent image segmentation to identify amyloid associated with either ocular or brain conditions.

* * * * *